Figure 1:
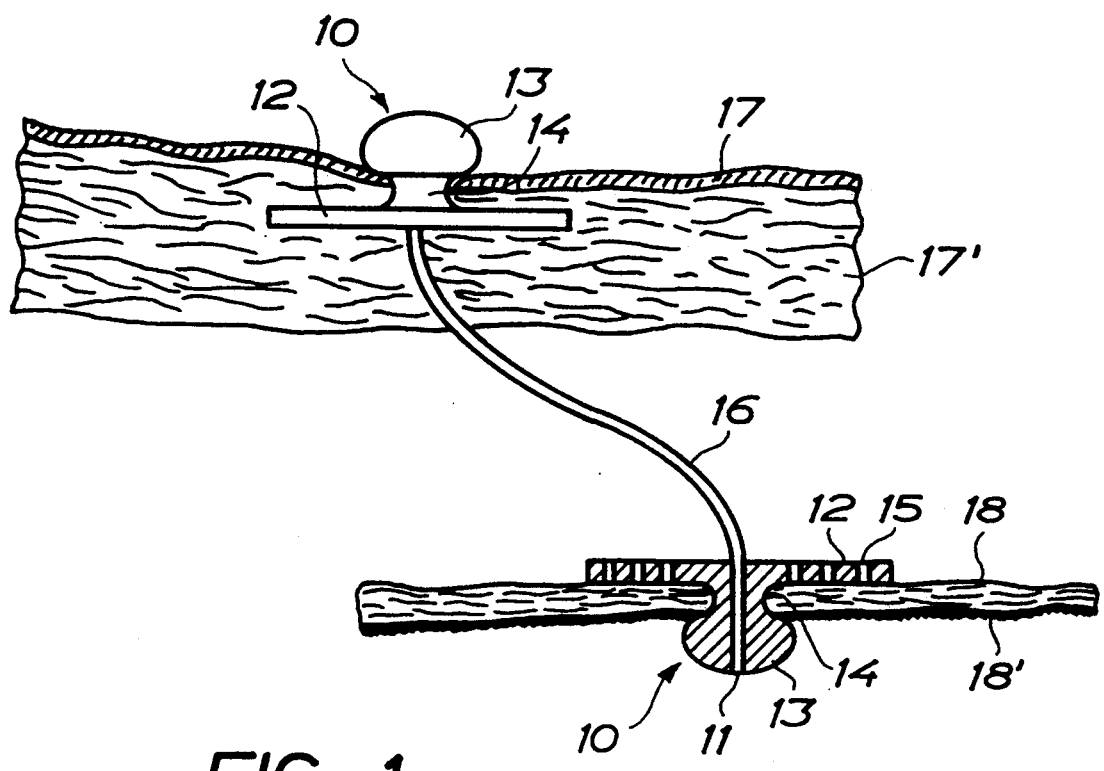

United States Patent
Lundgren

Patent Number: 5,425,761
Date of Patent: Jun. 20, 1995

[54] IMPLANT WITH A THROUGH PASSAGE

[76] Inventor: Dan Lundgren, Kyrkvägen 5, S-430 80 Hov∪s, Sweden

[21] Appl. No.: 64,093
[22] PCT Filed: Nov. 21, 1990
[86] PCT No.: PCT/SE91/00795
  § 371 Date: Jul. 7, 1993
  § 102(e) Date: Jul. 7, 1993
[87] PCT Pub. No.: WO92/09314
  PCT Pub. Date: Jun. 11, 1992

[30] Foreign Application Priority Data
  Nov. 21, 1990 [SE] Sweden ................ 9003718

[51] Int. Cl.⁶ ............................................. A61F 2/02
[52] U.S. Cl. ............................... 623/11; 623/12; 604/174; 606/155; 606/153
[58] Field of Search .............. 604/175, 8; 623/12, 623/11; 606/151, 153, 155

[56] References Cited
U.S. PATENT DOCUMENTS

| | | | |
|---|---|---|---|
| 3,461,869 | 8/1969 | Hargest | 604/175 |
| 3,663,965 | 5/1972 | Lee, Jr. et al. | 604/175 X |
| 3,818,511 | 6/1974 | Goldberg et al. | 623/12 X |
| 4,217,664 | 8/1980 | Faso | 623/12 X |
| 4,534,761 | 8/1985 | Raible | 623/12 X |
| 4,623,348 | 11/1986 | Feit | 623/12 X |
| 4,704,126 | 11/1987 | Baswell et al. | 623/12 X |
| 4,781,176 | 11/1988 | Ravo | 623/12 X |
| 4,781,694 | 11/1988 | Branemark et al. | 604/175 |
| 4,854,316 | 8/1989 | Davis | 623/12 X |
| 4,886,502 | 12/1989 | Poirier et al. | 604/175 |
| 4,897,081 | 1/1990 | Poirier et al. | 604/175 |
| 4,946,444 | 8/1990 | Heimke et al. | 604/175 |
| 4,976,735 | 12/1990 | Griffith et al. | 623/12 |
| 5,084,024 | 1/1992 | Skinner | 604/175 |
| 5,147,374 | 9/1992 | Fernandez | 623/12 X |
| 5,234,408 | 8/1993 | Griffith | 623/12 X |
| 5,242,415 | 9/1993 | Kantrowitz et al. | 604/175 |

FOREIGN PATENT DOCUMENTS 9114404 10/1991 WIPO ................ 623/11

Primary Examiner—David H. Willse
Attorney, Agent, or Firm—Joseph C. Mason, Jr.; Ronald E. Smith

[57] ABSTRACT

Implant with through passage (11) and intended to be applied as a through passage in the skin or in a membrane of the human body. The implant comprises a tubular body (10) provided with a radially protruding circular protruding flange (12), the perforation of flange (12) as least closest to the tubular body comprising slots (15) extending in the peripherical direction of the flange.

12 Claims, 2 Drawing Sheets

IMPLANT WITH A THROUGH PASSAGE

The present invention refers to an implant with a through passage and is intended to be applied as a passage through the skin or a membrane of the human body, the implant comprising a tubular body provided with a radially protruding circular perforated flange.

Implants of this type are disclosed e.g. in DE-A-26 45 990, U.S. Pat. Nos. 4,217,664, 3,663,965, EP-A1-0 367 357 and WO 87/06122. In all those cases, the flange is intended to be disposed under the skin. According to for example EP-A1-0 367 357 and WO 87/06122 the flange is disposed in the connective tissue under the skin in order to permit the growth of connective tissue through the perforation of the flange for anchoring of the implant. For the purpose of preventing downward epithelial growth around the implant and thus preventing the rejection of the implant the tubular body is arranged, according to WO 87/06122, with grooves which are delimited between perforated flanges in order to permit the growth of connective tissue into these grooves and thus preventing the downward growth of the epithelial layer along the tubular body.

The object of the invention is to bring about an implant of the above mentioned type, which combines great bearing capacity, i.e. large bearing surface of the flange, with good stability, i.e. good retention of the flange due to growth of the surrounding connective tissue into said flange, the downward epithelial growth at the same time being prevented by the growth of connective tissue into the flange. The implant according to the invention is adapted to be used as a passage through the skin in order to be accessible from the outside to the interior of the organism through the passage in the tubular body, but it may also advantageously be used as a passage in a membrane, for example the peritoneum, the intestinal wall or other membranes of body cavities in the organism.

Figure 2:
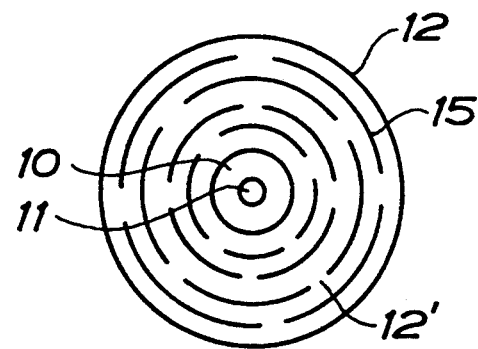
Figure 3:
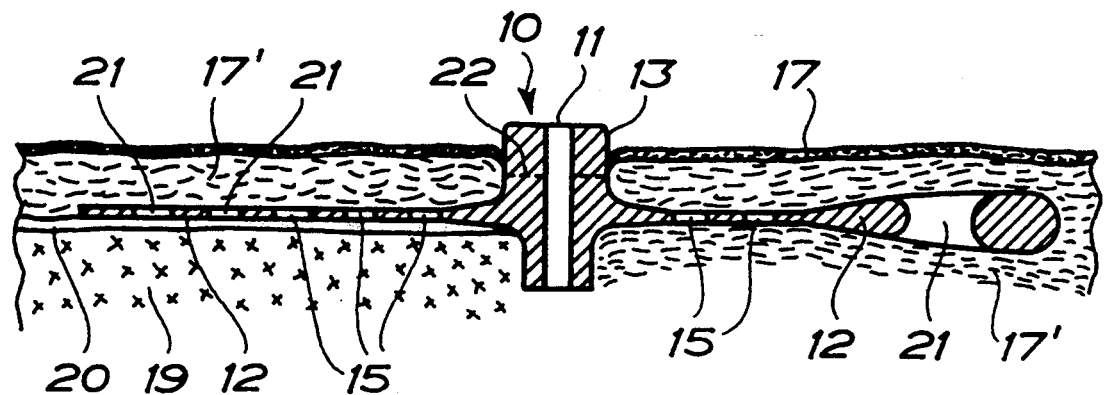
Figure 4:
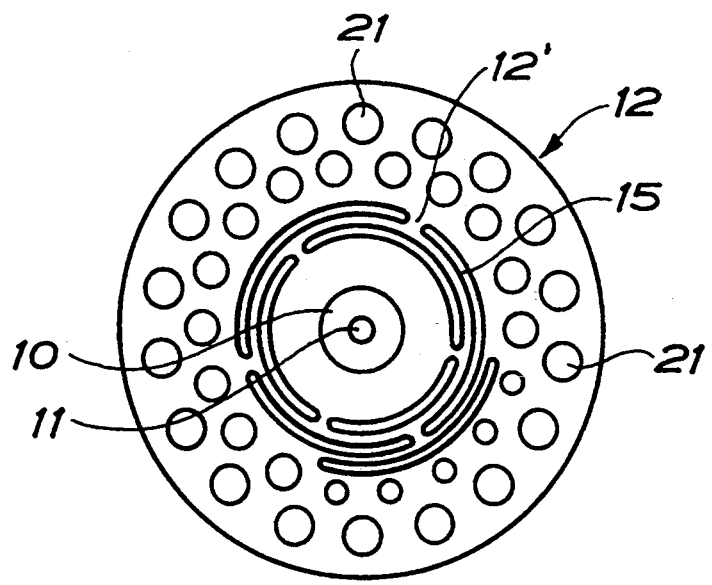

In order to further explain the invention reference is made to the accompanying drawing, in which FIG. 1 is a side view and a sectional view which shows the use of the implant according to the invention partly as a passage through the skin and partly as a passage through e.g. an intestinal mucous membrane in order to achieve a connection from the outside to the interior of the intestine, FIG. 2 is a plan view of the flange on the implant, FIG. 3 is an axial sectional view of a practical embodiment according to the invention arranged as a passage through the skin, the left half of the figure showing the implant with bone support and the right half showing the implant with soft-tissue support, and FIG. 4 is a plan view of the implant in FIG. 3.

The implant should be made of a biocompatible material, for example titanium or a suitable plastic. It comprises, according to FIGS. 1 and 2, a body 10 having a through channel 11. One end the body forms a circular or disc-shaped flange 12 whereas the other end forms an enlarged ball-shaped or bulbous portion 13 which can be more or less spherical but also may be mushroom-shaped. This portion connects to the flange at a circular neck 14 with a concavely rounded surface.

The flange is perforated and the perforation consists of slots 15 which extend concentrically in the circumferential direction of the flange and which overlap each other or are arranged one upon the other as shown in FIG. 2. As few bridges 12' as possible should be arranged between the slots in every ring of slots; at least three bridges should be provided, however, for strength reasons.

In FIG. 1 two identical implants are connected with each other by a catheter 16, one implant forming a passage in the skin 17 while the other implant forms a passage in for example an intestinal wall 18 with an intestinal mucous membrane 18', the implant with the catheter in between forming a permanent connection from the outside to the interior of the intestine for sampling the contents of the intestine or for supplying medicine or the like to the intestine. That implant which forms the passage through the skin has its flange 12 located in the connective tissue under the skin in order to allow growth of connective tissue through the perforation into the flange for anchoring the implant. By this inward growth, however, and above all in the area adjacent to the body 10, an effective barrier against downward growth of the epithelial layer of the skin is obtained without the need of providing special means for this purpose. Rejection of the implant could be caused by the downward growth of the epithelial layer. In order to make the flange fulfil the mentioned twofold function of forming an anchorage means and preventing epithelial downward growth, the length of the neck, on the basis of what has been found, should not be greater than 5 mm, preferably 3 mm. Due to this, the slots 15 closest to the body 10 are disposed at a distance of 3-5 mm from the surface of the skin or the intestinal mucous membrane, respectively, which means that a barrier of connective tissue will have the time needed to establish itself by inward growth of the connective tissue through the flange before the epithelial layer or the intestinal mucous membrane, respectively, has managed to grow down to the slots located closest to the body 10. The ball-shaped portion should be as low as possible in order not to disturb adjacent organs. It is suitably bright polished in order to exhibit the lowest possible surface tension, whereby the mucous membrane or the skin is prevented from growing over the implant.

The implant in the intestinal wall 18 is arranged with its flange against the outside of the intestinal wall. It can initially be retained in the intestinal wall by punching a hole in the intestinal wall 18, which has a smaller diameter than the ball-shaped portion 13 and then by pressing the portion through the intestinal wall while elastically enlarging the hole. By the inward growth of surrounding soft tissue into the flange the implant in the intestinal wall will be securely anchored to said wall. By bright polishing the ball-shaped portion 13 overgrowth of this portion is prevented, which is extremely important since the implant is not accessible from the outside for removal of possible overgrowth on the inside of the intestinal wall. The ball-shaped portion 13 has to be as low as possible here in order not to form an obstruction in the abdominal cavity etc. However, it has to rise at least 1 mm above the mucous membrane 18', preferably somewhat more.

In the practical embodiment of the implant according to the invention, which is shown in FIGS. 3 and 4, the implant is arranged as a passage through the skin in the left half of FIG. 3 with bone support and in the right half of FIG. 3 with soft-tissue support. The body 10 is here made cylindrical. When the implant has bone support according to the left half of FIG. 3, the circular flange 12 is made very thin and its thickness should lie between 0.05 and 3 mm, preferably about 0.2 mm. The flange may be disposed either on the top of the periosteum 20 of the bone 19 or inserted between the bone and the periosteum. In the right half of FIG. 3 the flange lies solely in the connective tissue 17'. In this case the flange is made very thin in the area of the slots 15, i.e., as thin as the flange in the left half of the figure, while the flange, radially outward of the slots may be thicker and may gradually increase to greater thickness. In this part of the flange through holes 21 are arranged instead of slots. By making the flange very thin in the area of the slots closest to the body 10 the connective tissue 17' surrounding the flange can grow as fast as possible through the slots into the flange for healing up the implant due to the fact that the connective tissue on top of the flange through the slots immediately meets and by growth joins the connective tissue under the flange. All edges of holes and slots and of the periphery of the flange should be softly rounded in order not to have a cutting effect and thus causing irritation in the tissue.

In a suitable embodiment of the invention the distance between the body 10 and the closest located slots should be 3–5 mm, the slots having a width of about 1 mm and the distance between them also being about 1 mm. The bridges 12' between the slots in one and the same ring of slots is suitably about 1 mm and, for strength reasons there should be at least three such bridges in each ring. The width of the slots and the distance between the slots, respectively, should be greater than 30 μm and suitably within the range of 0.1–2 mm. The thickness of the material in the thinner part of the flange should be between 0.05–3 mm and is suitably about 0.2 mm. The holes 21 radially outwardly of the slots have suitably a diameter of about 2 mm and the outermost portion of the flange, that portion which lies between the periphery of the flange and the outermost row of holes 21, should have a thickness and a width between 1–3 mm. It is especially important that this portion is softly rounded for the reasons mentioned above. The flange 12 may have a diameter which lies between 6–36 mm whereas the diameter of the body 10 lies between 1–16 mm.

Of course, the connective tissue will grow through the flange not only into the slots where it is important to have a rapid inward growth in the area closest to the body 10 in order to prevent downward growth of the epithelial layer 17 and the intestinal mucous membrane 18', respectively, but the connective tissue will, of course, also grow through the holes 21, though somewhat slower. The number of holes and the diameter thereof should be chosen in such a way that a balance between the bearing capacity of the flange, which means that the flange shall have a large bearing surface (the nonperforated part of the flange), and the stability of the flange, which is dependent on that retention of the implant which is attained by the inward growth of the connective tissue into the holes 21.

In FIG. 3 a transverse dashed line 22 is drawn on the body 22, which indicates a parting line. By manufacturing the upper portion of the body 10 as a separate part which may be detachably attached to the remaining part of the body, a two-step method can be applied when inserting the implant by surgery according to FIG. 3. With the detachable part of the body 10 removed, the implant is inserted by surgery and the skin or the mucous membrane, respectively, is allowed to grow over the implant. After this first step and after healing during inward growth of connective tissue into the slots, a perforation of the skin or the mucous membrane, respectively, is accomplished in a second step and the separate upper portion of the body 10 is applied on the already ingrown part of the implant and is allowed to protrude through the perforation. The epithelial layer of the skin of the mesothelial layer of the mucous membrane, respectively, is now effectively prevented from growing downwards along the body 10 during the continous inward growth of connective tissue into the holes 21 into the flange, since the necessary inward growth of connective tissue into the slots around the body has already taken place in order to prevent downward epithelial growth. The same method can be applied when inserting the implant by surgery for example in the abdominal or intestinal wall.

In order to further render the preventing function of downward epithelial growth by the connective tissue more effective, the total area of the flange (including both the upper side and under side, but above all the slotted area and the area between the slotted area and the tubular body) should be designed with a topography consisting of grooves, holes etc. having a width or a diameter of 1–8 μm, preferably 2–4 μm, and with a relative distance of likewise 1–8 μm, preferably 2–4 μm. This is suitably achieved by a known so called litographic technique. By this surface topographical arrangement the fibroblasts of the connective tissue will exceptionally intimately adhere to the surface of the flange thereby further preventing the epithelial downward growth.

I claim:

1. An implant, comprising:
    a first part of bulbous configuration;
    a second part of flat, disc-shaped configuration;
    a neck interconnecting said first and second parts, said neck having a diameter less than respective diameters of said first and second parts;
    a central throughbore formed in said first part, said neck, and said second part; and
    a plurality of sets of concentric, radially equidistantly spaced apart slots formed in said second part;
    each of said slots having a predetermined circumferential extent, there being a plurality of circumferentially spaced apart slots formed in each set of slots.

2. The implant of claim 1, wherein the slots in each set of slots are staggered as between radially contiguous sets of slots so that a preselected imaginary radially extending straight line emanating from said central throughbore alternately passes through slots and unslotted parts of said second part.

3. The implant of claims 1 or 2, wherein said second part has a thickness between 0.05 and 3.0 mm.

4. The implant of claims 1 or 2, wherein said slots have a radial width between 0.1 and 2.0 mm.

5. The implant of claims 1 or 2, wherein radially contiguous slots are spaced apart by a radial distance between 0.1 and 2.0 mm.

6. The implant of claims 1 or 2, wherein each of said slots have rounded edges and wherein said second part has a rounded peripheral edge.

7. The implant of claims 1 or 2, wherein said neck has a length of about 3 mm.

8. An implant, comprising:
    a first part of bulbous configuration;
    a second part of flat, disc-shaped configuration;
    a neck interconnecting said first and second parts, said neck having a diameter less than respective diameters of said first and second parts;

a central throughbore formed in said first part, said neck, and said second part; and a plurality of sets of concentric, radially equidistantly spaced apart slots formed in said second part;

each of said slots having a predetermined circumferential extent, there being a plurality of circumferentially spaced apart slots formed in each set of slots; and a plurality of sets of concentric, radially spaced apart holes formed in said second part, radially outwardly of said slots 9. The implant of claim 8, wherein the slots in each set of slots are staggered as between radially contiguous sets of slots so that a preselected imaginary radially extending straight line emanating from said central throughbore alternately passes through slots and unslotted parts of said second part.

10. The implant of claim 9, wherein the holes in each set of holes are staggered as between radially contiguous sets of holes so that a preselected imaginary radially extending straight line emanating from said central throughbore alternately passes through holes and imperforate parts of said second part.

11. The implant of claim 8, wherein said slots, said holes, and a peripheral edge of said second part have rounded edges.

12. An implant, comprising:

a first part of tubular configuration;

said first part having an upper end and a lower end;

a second part of flat, disc-shaped configuration;

said second part being formed integrally with said lower end of said first part;

a central throughbore formed in said first part and said second part;

a plurality of sets of concentric, radially equidistantly spaced apart slots formed in said second part;

each of said slots having a predetermined circumferential extent, there being a plurality of circumferentially spaced apart slots formed in each set of slots;

said first part including an upper, detachable part.

* * * * *